United States Patent [19]
Kung

[11] Patent Number: 5,609,849
[45] Date of Patent: Mar. 11, 1997

[54] SEROTONIN (5-HT$_{1A}$) RECEPTOR LIGANDS AND IMAGING AGENTS

[75] Inventor: Hank F. Kung, Wynnewood, Pa.

[73] Assignee: The Trustees of the University of Pennsylvania, Philadelphia, Pa.

[21] Appl. No.: 209,985

[22] Filed: Mar. 11, 1994

[51] Int. Cl.$^6$ .......... A61K 51/04; C07D 401/00; C07D 403/00; C07D 241/02
[52] U.S. Cl. .......... 424/185; 424/189; 544/360; 544/295; 544/357; 544/225; 514/252
[58] Field of Search .......... 424/1.85, 1.89; 544/360, 295, 357; 514/252

[56] References Cited

U.S. PATENT DOCUMENTS

| | | | |
|---|---|---|---|
| 5,075,303 | 12/1991 | Cliffe et al. | 514/218 |
| 5,135,931 | 8/1992 | Carlier et al. | 514/252 |
| 5,166,157 | 11/1992 | Lavielle et al. | 514/255 |
| 5,169,845 | 12/1992 | Cliffe et al. | 514/212 |
| 5,177,078 | 1/1993 | Ward et al. | 514/253 |
| 5,364,849 | 11/1994 | Cliffe | 514/212 |
| 5,369,103 | 11/1994 | Cliffe | 514/211 |
| 5,382,583 | 1/1995 | Cliffe | 514/252 |
| 5,420,278 | 5/1995 | Cliffe | 544/392 |
| 5,430,033 | 7/1995 | Cliffe et al. | 514/254 |

FOREIGN PATENT DOCUMENTS

| | | |
|---|---|---|
| 0395312A2 | 10/1990 | European Pat. Off. |
| 0481744A1 | 4/1992 | European Pat. Off. |
| 0512755A2 | 11/1992 | European Pat. Off. |
| WO92/06082 | 4/1992 | WIPO |
| WO92/06960 | 4/1992 | WIPO |
| WO93/11122 | 6/1993 | WIPO |
| WO93/14076 | 7/1993 | WIPO |

OTHER PUBLICATIONS

Van Wijngaarden et al., J. Med. Chem., 30, 1987, 2099–2104.

Hillver et al., "(S)-5-Fluoro-8-Hydroxy-2-(dipropylamino)tetralin: A Putative 5-HT$_{1A}$–Receptor Antagonist [letter]", J. Med. Chem. 33: 1541–1544 (1990).

Raghupathi et al., "Analogues of the 5-HT$_{1A}$ Serotonin Antagonist 1-(2-Methoxyphenyl)-4-[4-(2-phthalimido)butyl] Piperazine with Reduced ]α$_1$-Adrenergic Affinity", J. Med. Chem. 34:2633–2638 (1991).

Glennon et al., "Arylpiperazine Derivatives as High-Affinity 5-HT$_{1A}$ Serotonin Ligands", J. Med. Chem. 31: 1968–1971 (1988).

Hjorth et al., "8-Hydroxy-2-(Di-N-Propylamino)Tetralin 8-OH-DPAT, A Potent and Selective Simplified Ergot Congener with Central 5-HT-Receptor Stimulating Activity", J. Neural Transmission 55: 169–188 (1982).

Zhuang et al., "Synthesis of (R,S) [Trans-8-Hydroxy-2-(N-n-propyl-N-3'-iodo-2'-propenyl amino]tetraline (trans-8-OH-PIPAT): A New 5-HT$_{1A}$ Receptor Ligand", J. Med. Chem. 36: 3161–3165 (1993).

Greuel and Glaser, "the Putative 5-HT$_{1A}$ Receptor Antagonists NAN-190 and BMY 7378 are Partial Agonists in the Rat Dorsal Raphe Nucleus In Vitro", Eur. J. Pharmacol 211: 211–219 (1992).

Fletcher et al., "WAY100135: A Novel, Selective Antagonist at Presynaptic and Postsynaptic 5-HT$_{1A}$ Receptors", Eur. J. Pharmacol. 237: 283–291 (1993).

(List continued on next page.)

Primary Examiner—John Kight
Assistant Examiner—Lara E. Chapman
Attorney, Agent, or Firm—Woodcock Washburn Kurtz Mackiewicz & Norris

[57] ABSTRACT

Compounds such as 4-(s'-methoxy)phenyl-[2'-N-2"-pyridinyl)-p-iodobenzamido]ethylpiperazine have affinity and specificity for serotonin 5-HT$_{1A}$ receptors.

6 Claims, 6 Drawing Sheets

OTHER PUBLICATIONS

Cliffe et al., "(S)-N-Tert-Butyl-3-(4-(2-methoxyphenyl)-piperazin-1-yl)-2-phenylpropanamide, (S)-WAY-100135): A Selective Antagonist at Presynaptic and Postsynaptic 5-HT$_{1A}$ Receptors", *J. Med. Chem.* 36: 1509–1510 (1993).

Fletcher, A., et al, "Silent 5-HT$_{1A}$ Receptor Antagonists: Utility As Research Tools and Therapeutic Agents," *TIPS* 4: 441–448 (1993).

Cliffe et al. "The Design of Selective 5-HT$_{1A}$ Receptor Antagonists". *206th ACS Meeting, MEDI Abs.* #30 (1990).

Chumpradit et al., "Iodinated Tomoxetine Derivatives as Selective Ligands for Serotonin and Norepinephrine Uptake Sites", *J. Med. Chem.* 35: 4492–4497 (1992).

Foreman et al., "Preclinical Studies on LY228729: A Potent and Selective Serotonin$_{1A}$ Agonist", *J. Pharm and Exp. Ther* 267: 58–71 (1993).

p-MPPI, 1a m-MPPI, 1b

SEROTONIN (5-HT$_{1A}$) RECEPTOR LIGANDS AND IMAGING AGENTS

GOVERNMENT SUPPORT

The work reported herein was supported at least in part by NIH NS-24538 and NIMH-48125.

FIELD OF THE INVENTION

This invention relates to novel compounds which display selective binding for serotonin (5-HT$_{1A}$) receptors, to methods of preparing such ligands, to methods of utilizing them as imaging agents, and to novel compounds useful as intermediates in the preparation of such ligands.

BACKGROUND OF THE INVENTION

Neural transmitters are chemicals in the brain that are used to send messages from one brain cell to another. Neurotransmitters bind to special receptor proteins in the membrane of nerve cells, like a key in a lock, triggering a chemical reaction within the cell. Serotonin (5-HT) is one form of neural transmitter.

The serotonin system in brain is an important neurotransmission network regulating various physiological functions and behavior including anxiety and affective states. Serotonin has been linked with depression and with other psychiatric disorders such as eating disorders., alcoholism, pain, anxiety, and obsessive-compulsive behavior. One of the serotonin receptor subtypes, 5-HT$_{1A}$, plays an important function as the somatodendretic autoreceptor (presynaptic) in the dorsal raphe nucleus and as a postsynaptic receptor for 5-HT in terminal field areas.

A number of agonists and antagonists for 5-HT$_{1A}$ receptors are reported in the literature (Hillver et al., "(S)-5-Fluoro-8-Hydroxy-2-(dipropylamino)tetralin: A Putative 5-HT$_{1A}$-Receptor Antagonist [letter]" *J. Med. Chem.* 33: 1541–1544 (1990); Raghupathi et al., "Analogues of the 5-HT$_{1A}$ Serotonin Antagonist 1-(2-Methoxyphenyl)-4-[4-(2-phthalimido)butyl]Piperazine with Reduced Alpha-Adrenergic Affinity" *J. Med. Chem.* 34:2633–2638 (1991); Glennon et al., "Arylpiperazine Derivatives as High-Affinity 5-HT$_{1A}$ Serotonin Ligands" *J. Med. Chem.* 31:1968–1971 (1988)). Examples include 8-hydroxy-2-(N,N-di-n-propyl)aminotetralin (8-OH-DPAT), (Hoyer et al., "Molecular Pharmacology of 5-HT1 and 5-HT2 Recognition Sites in Rat and Pig Brain Membranes: Radioligand Binding Studies with [3H]5-HT, [3H]8-OH-DPAT, (−)[125I]Iodocyanopindolol, [3H]Mesulergine and [3H]Ketanserin" *Eur. J. Pharmacol.* 118:13–23 (1985); Hjorth et al., "8-Hydroxy-2-(di-n-propylamino)tetralin 8-OH-DPAT, A Potent and Selective Simplified Ergot Congener with Central 5-HT Receptor Stimulating Activity" *J. Neural. Transmission* 55: 169–188 (1982)) (R,S)trans-8-hydroxy-2-[N-n-propyl-N-(3'-iodo-2'-propenyl)]aminotetralin, ((R,S)trans-8-OH-PIPAT), (Zhuang et al., "Synthesis of (R,S)trans-8-Hydroxy-2-(N-n-propyl-N-3'-iodo-2'-propenyl aminotetraline (trans-8-OH-PIPAT): A New 5-HT$_{1A}$ Receptor Ligand", *J. Med. Chem.* 36:3161–3165 (1993)), and 1-(2-methoxyphenyl)-4-[4-(2-phthalimido)butyl]piperazine (NAN-190) (Greuel et al., "The Putative 5-HT$_{1A}$ Receptor Antagonists NAN-190 and BMY 7378 are Partial Agonists in the Rat Dorsal Raphe Nucleus In Vitro", *Eur. J. Pharmacol* 211: 211–219 (1992)). NAN-190 displayed high 5-HT$_{1A}$ affinity (Ki=0.6 nM) and with an equal potency for the α1 receptor. Replacement of the phthalimide moiety by substituted benzamides or acyl moieties provides ligands with high binding affinity and selectivity. One such agent, 4-[4-(1-adamantanecarboxamido)-butyl]1-(2-methoxyphenyl)piperazine, was found to bind to 5-HT$_{1A}$ receptor with high affinity (Kd=0.4 nM) and was devoid of binding affinity to other receptors.

Recently, a new arylpiperazine derivative, N-tert-butyl-3-(4-(-2-methoxyphenyl)piperazin-1-yl)-2-phenylpropionamide, (5)-WAY 100135, was reported as a selective antagonist at both somatodendritic and postsynaptic receptor (IC$_{50}$=15 nM, rat hippocampal membranes) (Fletcher et al., "A Novel, Selective Antagonist at Presynaptic and Postsynaptic 5-HT$_{1A}$ Receptors", *Eur. J. Pharmacol.* 237:283–291 (1993); Cliffe et al., "(S)-Nj-Tert-Butyl-3-(4-(2-methoxyphenyl) - piperazin-1-yl)-2phenylpropanamide, (S)-WAY-100135: A Selective Antagonist at Presynaptic and Postsynaptic 5-HT$_{1A}$ Receptors", *J. Med. Chem.* 36: 1509–1510 (1993) Fletcher, A., et al., "Silent 5-HT$_{1A}$ Receptor Antagonists: Utility As Research Tools and Therapeutic Agents," *TIPS* 4:441–448 (1993)). A related compound, 4-(2'-methoxy-) phenyl-1-[2'-(N-2"-pyridinyl)-cyclohexylamido-]ethylpiperazine, WAY 100635, displayed even higher binding affinity (IC$_{50}$=2.2 nM, rat hippocampal membranes) with high selectivity (Cliffe et al., "The Design of Selective 5-HT$_{1A}$ Receptor Antagonists. 206th ACS Meeting, MEDI Abs. #30 (1990)).

It is not only desirable to find new compounds selective to 5-HT$_{1A}$ receptors for possible pharmacological activity; such specific ligands are desired as they may be useful for monitoring the effectiveness of drugs and substances which affect brain chemistry. For instance, it is highly desirable to be able to gauge the biochemical effects of drugs administered for blocking the patient's serotonin receptors. If too little of the drug is administered, the desired blockade does not occur, and if too much of the drug is administered, there can be severe side effects.

New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer)/are measured. These emissions are indicative of the number and degree of occupancy of blocking of the neuroreceptors. The number of neuroreceptors and the degree of occupancy or blocking is calculated utilizing a mathematical model, and compared with an intra-person or inter-person control, to determine the degree of drug.-response. Further treatment of the patient with drugs is based upon the comparisons made. For these methods to be useful, however, a ligand which has high affinity and specificity for the desired receptor is required.

There is, therefore, a clear need for potent and selective ligands for 5-HT$_{1A}$ receptors which ligands may not only have pharmacological activity but which can also be labelled with high specific activity to aid the progress of understanding the pharmacological function and regulation of the receptor subtype in its native state.

SUMMARY OF THE INVENTION

Test results indicate that the novel compounds of Formula I are highly selective for the serotonin (5-HT$_{1A}$) receptor.

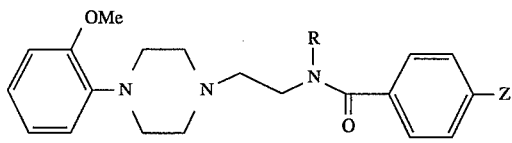

where

Z is selected from the group consisting of iodine, bromine and fluorine;

R is selected from the group consisting of

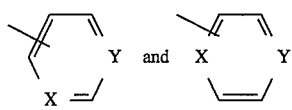

X and Y are independently selected from the group consisting of N and CH, provided that at least one of X and Y is N;

and pharmaceutically acceptable salts thereof.

Tests indicate that compounds of Formula I are highly selective for the serotonin 5-HT$_{1A}$ receptor and should therefore have pharmacological activity associated with the binding of that receptor or, if appropriately radiolabelled, should possess utility as imaging agents for evaluation of that receptor. Tests also indicate that quite unexpectedly, the para-substituted compounds of this invention have significantly higher uptake in the hippocampal region of the brain, where 5-HT$_{1A}$ receptor density is high, than the analogous meta-substituted compounds.

This invention therefore relates to the novel compounds of Formulas I, to methods of preparing them and to methods of utilizing them as imaging agents for the evaluation of 5-HT$_{1A}$ receptors. This invention further relates to novel compounds of Formula II which are useful as intermediates for preparing radiolabelled compounds of Formula I.

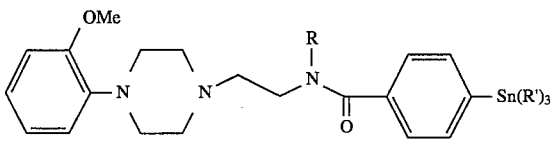

where R, X and Y are as defined above and where R' is a $C_1$–$C_5$ alkyl.

DETAILED DESCRIPTION OF THE INVENTION

Figure 1A:
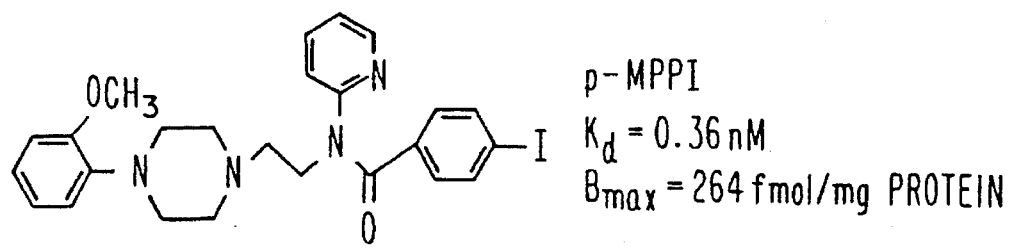
FIGS. 1a, 1b, and 1c provide saturation and scatchard plots of [$^{125}$I]p-MPPI in rat hippocampus tissue homogenates. Squares represent total; circles represent specific; triangles represent nonspecific binding. Binding assays were carried out at 37° C. for 15 min. (Buffer: 50 mM Tris-HCl, pH 7.4 with 2 mM MgCl$_2$; 10 μM 5-HT was used to define nonspecific binding). The plots were constructed from values obtained by a non-linear least squares analysis with the program LIGAND; $K_d$=0.36 nM; $B_{max}$=264 fmol/mg of protein.

Synthesis of iodinated arylpiperazine derivatives of this invention may be achieved by reactions described in Scheme 1.

Scheme 1

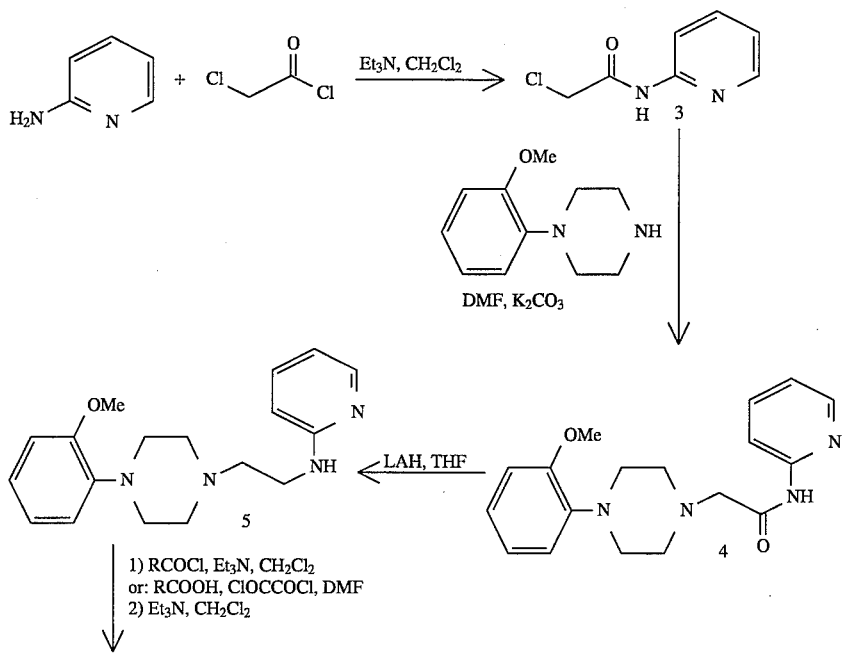

-continued
Scheme 1

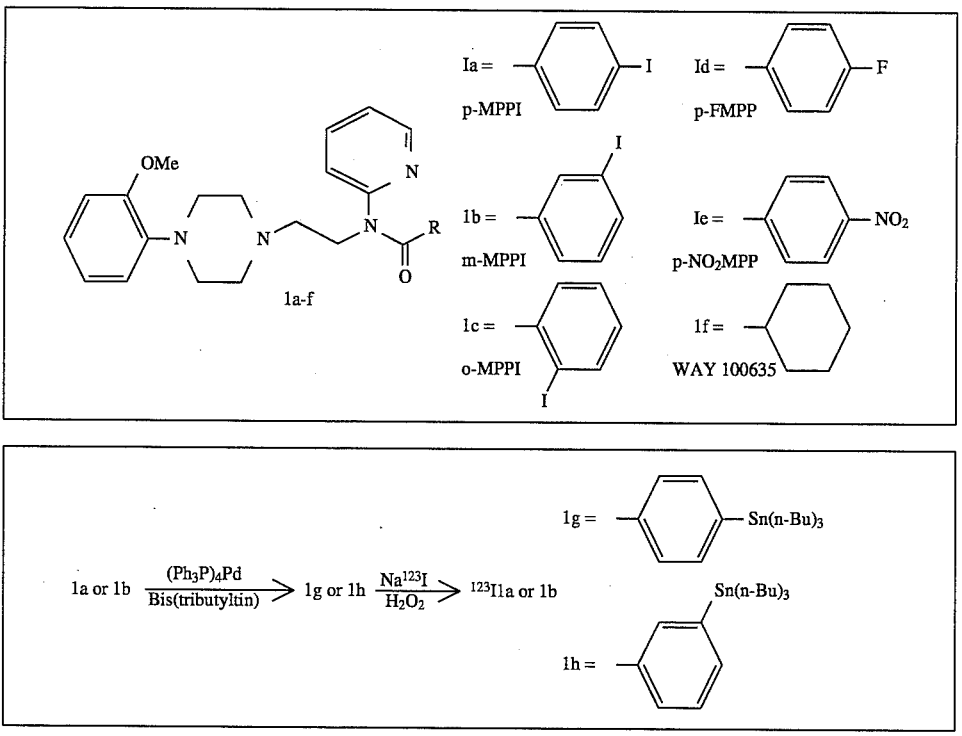

Two-step preparation of the key intermediate compound 5 is relatively straightforward and can result in high overall yield. Coupling of the acyl groups with the arylpiperazine, 5, can be accomplished either with an acyl chloride in the presence of triethylamine or by the use of acids with oxalyl chloride in DMF.

In the acyl chloride method, a solution of acyl chloride in $CH_2Cl_2$ may be added dropwise at 0° C. to a solution of the appropriate aryl piperazine 5 and Et3N in $CH_2Cl_2$ is added. The mixture is stirred at room temperature for approximately one hour. Water is added and the mixture is extracted with $CH_2Cl_2$. The combined organic layers are dried and evaporated to give the crude product which can be purified by PTLC (EtOAc as developing solvent) or MPLC (EtOAc as eluent) to give the desired pure product.

In the acid method, oxalyl chloride may be added to a mixture of acid and DMF in $CH_2Cl_2$ at 0° C. in an ice bath. The mixture is stirred at 0° C. for 30 minutes. Solvent and the excess oxalyl chloride are removed on vacuum, and the residue is dissolved in $CH_2Cl_2$ which is added to a solution of amine and Eton in $CH_2Cl_2$ at 0° C. The mixture is stirred at room temperature for one hour. The desired pure product can be obtained using the general procedure described above.

To produce a tri-n-butyltin derivative for radiohalogenation, bis(tributyltin) is added neat to a mixture of the appropriate iodo compound and $(Ph_3P)_4Pd$ in $Et_3N$. The mixture is stirred at 90° C. for sixteen hours. $Et_3N$ is removed on vacuum and the residue is purified by PTLC (EtOAc as developing solvent) to give pure product.

Radioiodination with I-125 (no carrier added, $Na^{125}I$) can be carried out starting with the corresponding tri-n-butyltin derivative (1 g), with hydrogen peroxide as the oxidant. Radiohalogenation with other isotopes is carried out in an analogous manner.

With the information provided above, one skilled in the art would be able to select the appropriate starting materials and prepare any of the claimed compounds of this invention.

When the compounds of this invention are to be used as imaging agents, they must be labelled with suitable radioactive halogen isotopes. Although $^{125}I$-isotopes are useful for laboratory testing, they will generally not be useful for actual diagnostic purposes because of the relatively long half-life (60 days) and low gamma-emission (30–65 Key) of $^{125}I$. The isotope $^{123}I$ has a half life of thirteen hours and gamma energy of 159 KeV, and it is therefore expected that labeling of ligands to be used for diagnostic purposes would be with this isotope. Other isotopes which may be used include $^{131}I$ (half life of 2 hours). Suitable bromine isotopes include $^{77}Br$ and $^{76}Br$. For use in PET imaging, the compounds will generally be labelled with a radioactive fluorine, $^{18}F$.

Pharmaceutically-acceptable salts of the compounds of this invention include the acid addition salts derived from nontoxic inorganic acids such as hydrochloric acid, nitric acid, phosphoric acid, sulfuric acid, hydrobromic acid, hydroiodic acid, phosphorous acid and the like. Also included are those salts derived from non-toxic organic acids such as aliphatic mono and dicarboxylic acids, phenyl-substituted alkanoic acids, hydroxy alkanoic and alkandioic acids, aromatic acids, and aliphatic and aromatic sulfonic acids.

Preferred compounds of this invention are those where, independently or in combination: (a) Z is a radioactive halogen isotope, and (b) R is pyridyl. More preferred compounds are those where, independently, (a) Z is a radioactive iodine isotope and (b) R is pyridyl. Specifically preferred compounds are 4-(2'-methoxy)phenyl-[2'-(N-2"-pyridinyl)-p-iodobenzamido]ethylpiperazine (p-MPPI) and its $^{125}I$-labelled analog.

Figure 1B:
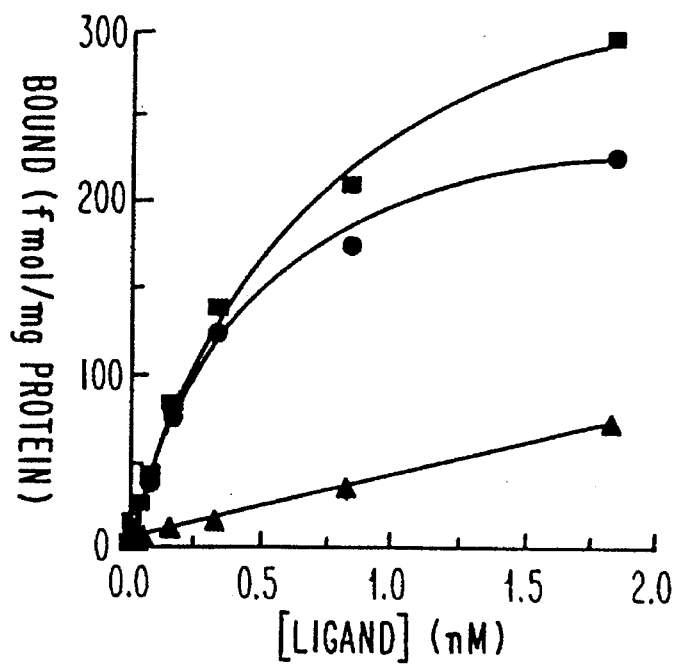
Figure 1C:
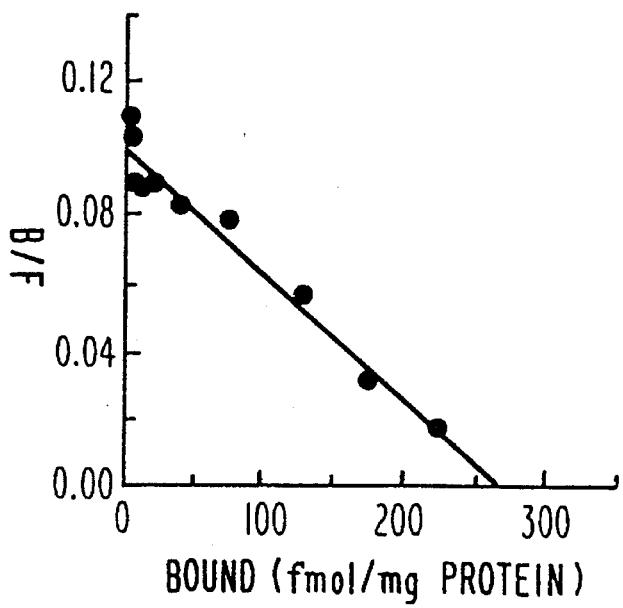
Figure 2A:
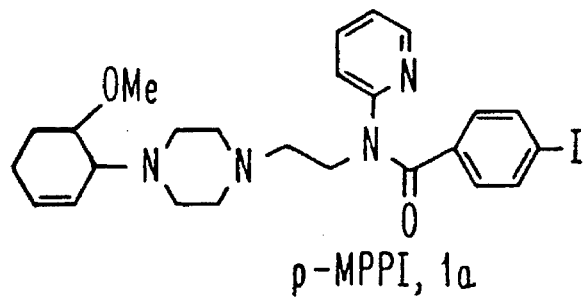
FIGS. 2a and 2b and FIGS 3a and 3b illustrate the regional brain uptake in rats of [$^{125}$I]p-MPPI and m-MPPI, respectively. HP: hippocampus; CB: cerebellum; HY: hypothalamus; CX: cortex; ST: striatum.
Figure 2B:
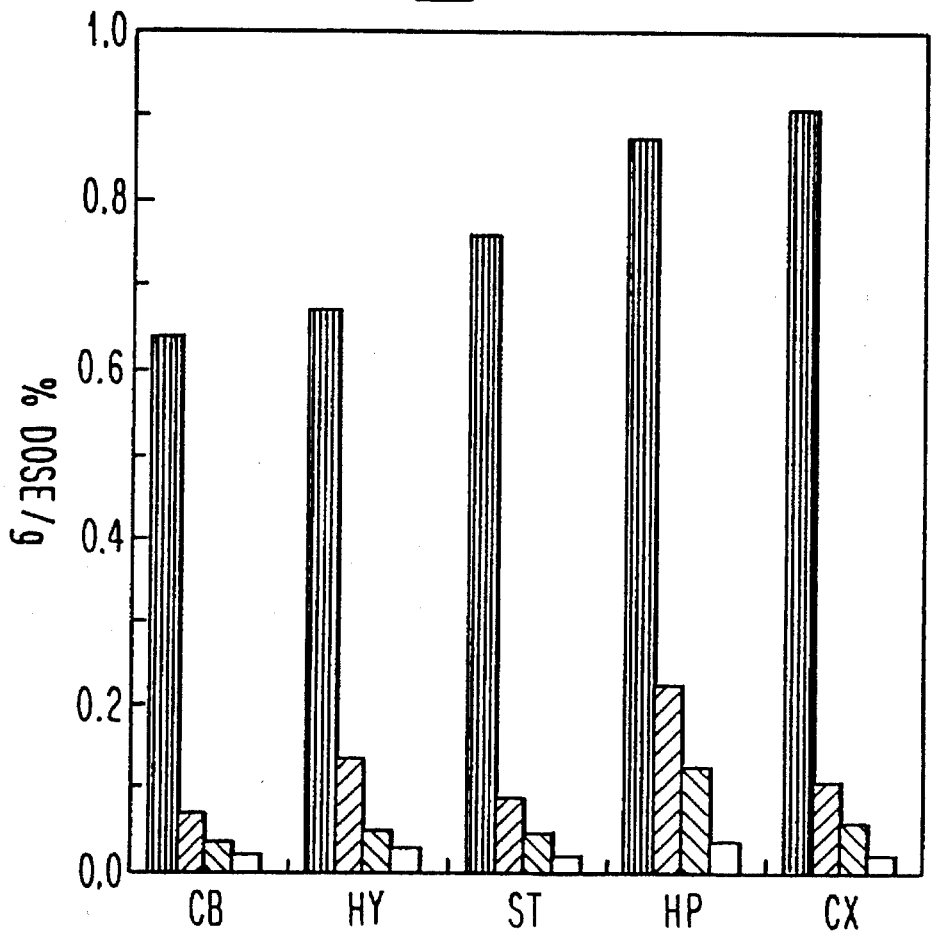
Figure 2C:
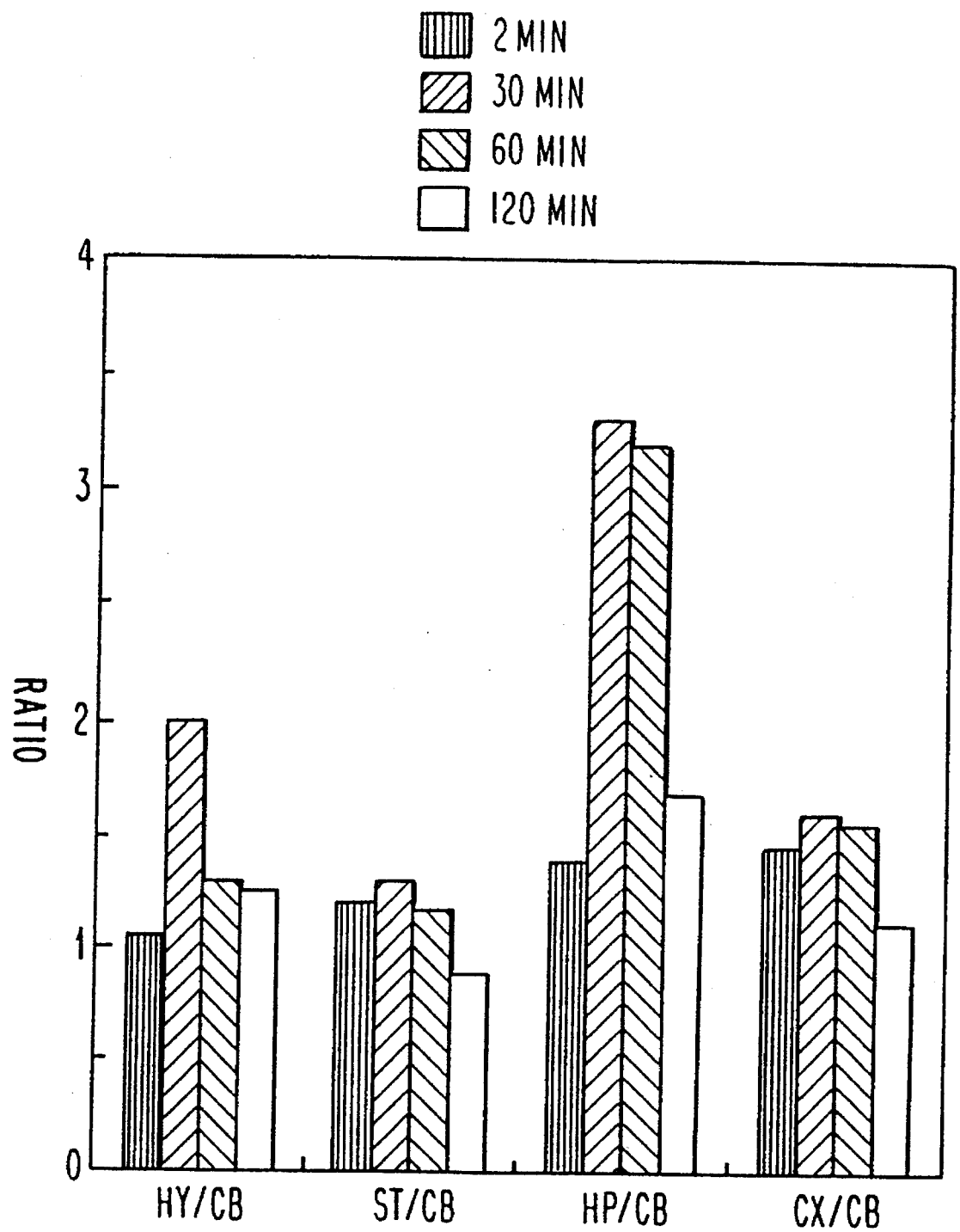
Figure 3A:
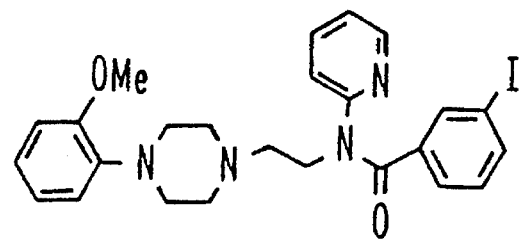
Figure 3B:
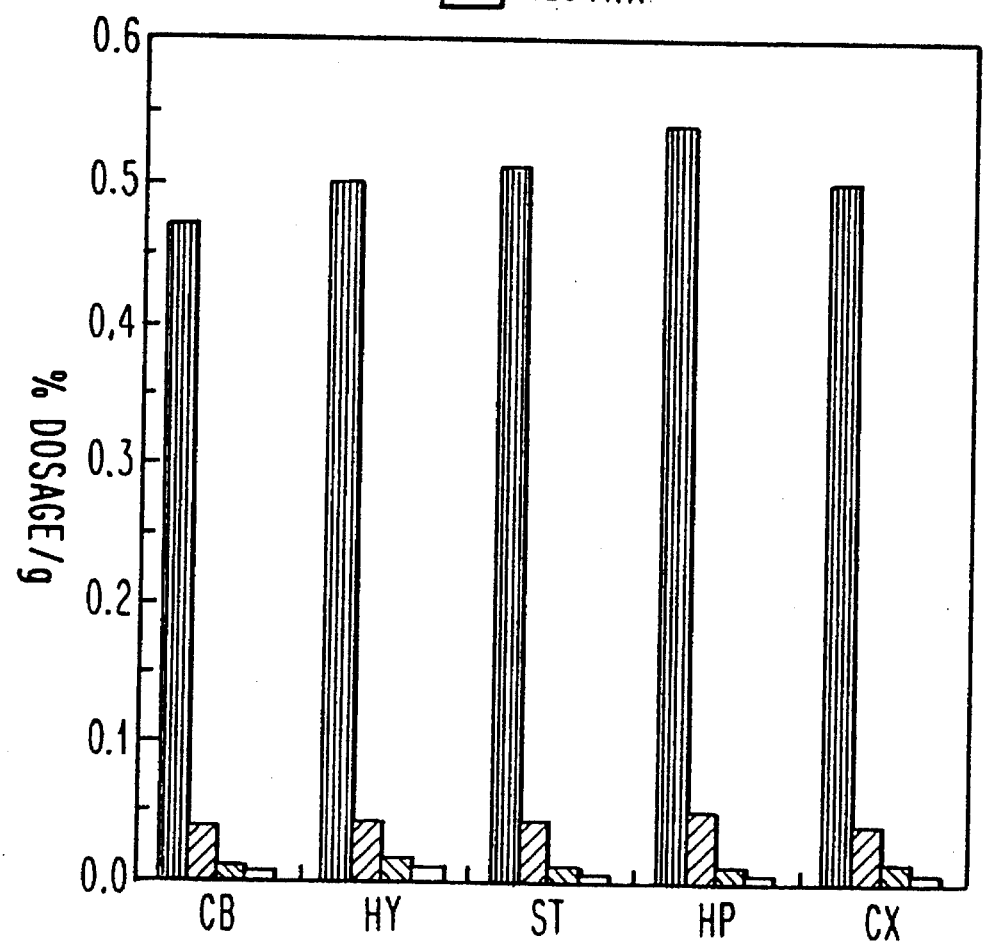
Figure 3C:
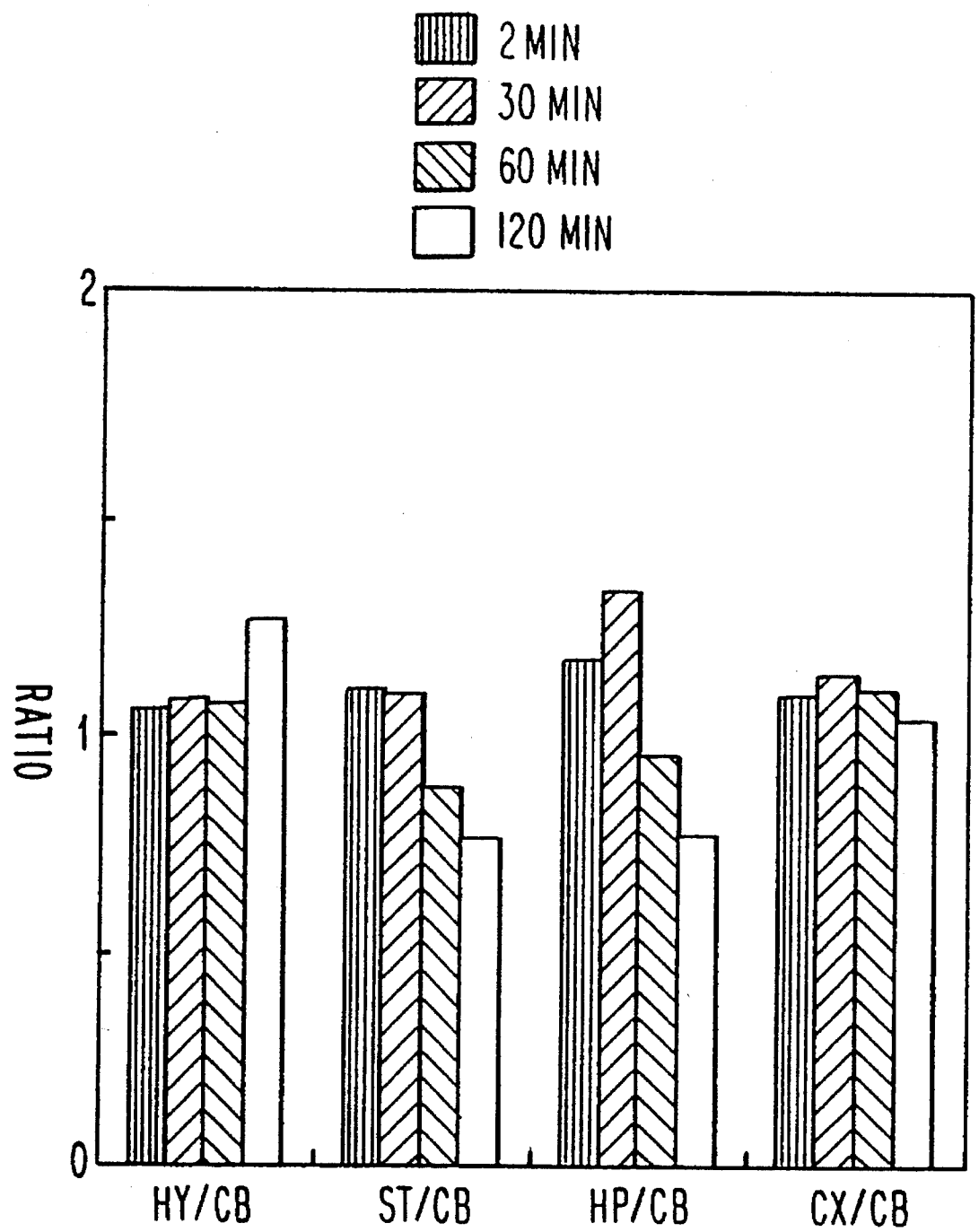

Compounds within the scope of FIGS. 1a, 1b, and 1c are useful, when labelled radioactively, as imaging agents as hereinafter described. Non-radioactive compounds of FIG. 1 may also have therapeutic utility and are additionally useful as intermediates for preparing radioactively labelled compounds, as shown in Scheme I.

Specific examples of compounds within the scope of this invention are illustrated in Table A.

TABLE A

[Structure: 2-methoxyphenyl-piperazine-CH₂CH₂-N(R)-C(O)-phenyl-Z]

| R | Z |
|---|---|
| 2-pyridyl | I |
| 3-pyridyl | I |
| 4-pyridyl | I |
| 2-pyridyl | Br |
| 3-pyridyl | Br |
| 4-pyridyl | Br |
| 2-pyridyl | $^{77}Br$ |
| 3-pyridyl | $^{77}Br$ |
| 4-pyridyl | $^{77}Br$ |
| 2-pyridyl | $^{76}Br$ |
| 3-pyridyl | $^{76}Br$ |
| 4-pyridyl | $^{76}Br$ |
| 2-pyridyl | $^{18}F$ |
| 3-pyridyl | $^{18}F$ |
| 4-pyridyl | $^{18}F$ |
| 2-pyridyl | F |
| 3-pyridyl | F |
| 4-pyridyl | F |
| 2-pyridyl | $^{125}I$ |
| 3-pyridyl | $^{125}I$ |
| 4-pyridyl | $^{125}I$ |
| 2-pyridyl | $^{123}I$ |
| 3-pyridyl | $^{123}I$ |
| 4-pyridyl | $^{123}I$ |
| 2-pyridyl | $^{131}I$ |
| 3-pyridyl | $^{131}I$ |
| 4-pyridyl | $^{131}I$ |
| 2-pyrimidyl | I |
| 4-pyrimidyl | I |
| 5-pyrimidyl | I |
| 2-pyrimidyl | Br |
| 4-pyrimidyl | Br |
| 5-pyrimidyl | Br |
| 2-pyrimidyl | $^{77}Br$ |
| 4-pyrimidyl | $^{77}Br$ |
| 5-pyrimidyl | $^{77}Br$ |
| 2-pyrimidyl | $^{76}Br$ |
| 4-pyrimidyl | $^{76}Br$ |
| 5-pyrimidyl | $^{76}Br$ |
| 2-pyrimidyl | F |
| 4-pyrimidyl | F |
| 5-pyrimidyl | F |
| 2-pyrimidyl | $^{18}F$ |
| 4-pyrimidyl | $^{18}F$ |
| 5-pyrimidyl | $^{18}F$ |
| 2-pyrimidyl | $^{125}I$ |
| 4-pyrimidyl | $^{125}I$ |
| 5-pyrimidyl | $^{125}I$ |
| 2-pyrimidyl | $^{123}I$ |
| 4-pyrimidyl | $^{123}I$ |
| 5-pyrimidyl | $^{123}I$ |
| 2-pyrimidyl | $^{131}I$ |
| 4-pyrimidyl | $^{131}I$ |
| 5-pyrimidyl | $^{131}I$ |

Tests indicate that compounds of this invention, especially p-MPPI, demonstrate unique high affinity and selectivity toward serotonin 5-HT$_{1A}$ sites. When the compounds are labelled with a radioactive ion, such as $^{123}I$, the serotonin reuptake sites may be imaged by means such as PET and SPECT. Such imaging of the human brain may provide or suggest direct information on the location and quantitation of the 5-HT$_{1A}$. Direct assessment on the status of serotonin 5-HT$_{1A}$ receptor may provide evidence of how the selective 5-HT$_{1A}$ agonists regulate the receptor sites and may also be a diagnostic tool for individualizing the dosage for this class of antianxielytic agents. The compounds of this invention which are not radiolabelled will also bind to 5-HT$_{1A}$ sites, suggesting therapeutic utility or use in in vitro binding studies.

The radiolabelled compounds of this invention lend themselves easily to formation from materials which could be provided to users in kits. Kits for forming the imaging agents can contain, for example, a vial containing a physiologically suitable solution of an intermediate of Formula II in a concentration and at a pH suitable for optimal complexing conditions. The user would add to the vial an appropriate quantity of the radioisotope, e.g., Na$^{123}$I, an oxidant, such as hydrogen peroxide. The resulting labelled ligand may then be administered intravenously to a patient, and receptors in the brain imaged by means of measuring the gamma ray or photo emissions therefrom.

The following examples are provided to further illustrate this invention and are not intended to limit its scope. These examples illustrate the preparation of compounds within the scope of this invention as well as compounds prepared and tested for purpose of comparison.

In the following examples, proton NMR spectra were obtained on a Brukker AmX300 spectrometer. The chemical shifts were reported in ppm down field from the tetramethylsilane standard. Infrared spectra were recorded on a Mattson Polaris FT-IR spectrometer. Low and high resolution mass spectra were carried out on a VG mass spectrometer model ZAB-E. The elemental analyses were performed by Atlantic Microlabs, Inc., Atlanta, Ga.

EXAMPLE 1

Preparation of
4-(2'-methoxy)phenyl-1-(2'-pyridinylaminocarbonyl) methyl piperazine (Compound 4, Scheme 1)

To a solution of 2-amino-pyridine (0.94 g, 1 mmol) and Et$_3$N (1.9 mL, 1.2 eq) in CH$_2$Cl$_2$ (20 mL) was added chloroacetyl chloride (0.98 mL, 1.2 eq) in neat at 0° C. in an ice bath. The mixture was stirred at 0° C. for 1 hour, cold water (10 mL) was added and the organic layer was separated. The aqueous layer was extracted with CH$_2$Cl$_2$. The combined organic layer was dried, evaporated to give a grey solid, 3, (1.9g). A mixture of the crude product, 3, (1.08g, 0.63 mmol) obtained above, 1-(2'-methoxy-)piperazine (1.34 g, 1.1 eq), and K$_2$CO$_3$ (2.62 g, 3 eq) in DMF (12 mL) was stirred at room temperature for 15 hours and quenched with water (20 mL). The mixture was extracted with CH$_2$Cl$_2$, and the organic layer was dried, evaporated (DMF was removed by distillation under reduced pressure) to give a crude product which was purified by MPLC (Hex:EtOAc= 2:1) to give the product, 4, (1.45 g) in 78% yield (2 steps).

IR (film, $v_{max}$) 3400, 2900, 2800, 1600, 1500, 1250 cm$^{-1}$.

1H NMR (CDCl3,δ): 2.83 (4H, t, J =4.8 Hz, C$\underline{H}_2$ of piperazine ring), 3.18 (4H, br, C$\underline{H}_2$ of piperazine ring), 3.24 (2H, s, COC$\underline{H}_2$—), 3.87 (3H, s, C$\underline{H}$3O—), 6.87 (1H, d,d, J=7.8, 1.0 Hz, aromatic $\underline{H}$), 6.93 –7.07 (4H, m, aromatic $\underline{H}$), 7.71 (1H, d, d, d, J=8.1, 7.6, 1.9 Hz, aromatic $\underline{H}$), 8.26

(1H, d,d, J=8.3, 0.8 Hz, aromatic H), 8.31 (1H, d,d,d, J=4.9, 0.8, 0.8 Hz, aromatic H), 9.64 (1H, br, NH).

Alal. ($C_{18}H_{22}N_4O_2 \cdot \frac{1}{4}H_2O$): Calcd: C, 65.34; H, 6.85; N, 16.93; Found: C, 65.72; H, 6.88; N, 16.58.

EXAMPLE 2

Preparation of 4-(2'-methoxy) phenyl-1-[2'-(2''-pyridinyl)amino]ethyl piperazine (Compound 5, Scheme 1)

To a slurry of LAH (95 mg, 2.5 mmol) in THF (5 mL) was added a solution of starting material, 4, (255 mg, 0.78 mmol) in THF (5 mL) slowly and dropwise at room temperature under stirring. The mixture was then refluxed for 1 hour and cooled to room temperature. Water (0.1 mL), NaOH (1 M, 0.1 mL) and additional water (0.3 mL) were added successively and the mixture was stirred at room temperature for 10 minutes and filtered. The filtrate was dried and evaporated to give a thick oil, 5, (219 mg, 90% yield), which was pure enough to be used in the next reaction without further purification. The elementary analysis sample was obtained by PTLC ($CH_2Cl_2$:MeOH=93:7). IR (film, $v_{max}$): 3373, 2942, 2815, 1598, 1498, 1237, 1145, 1023 $cm^{-1}$.

1H NMR ($CDCl_3$, δ): 2.69 (6H, t, J=6.0 Hz, $NCH_2$—), 3.1 (4H br $NCH_2$—), 3.38 (2H, q, J=5.7 Hz $NHCH_2$—), 3.86 (3H, s, $CH_3O$), 5.10 (1H, br, NH—), 6.41 (1H, d,t, J=8.4, 0.8 Hz, aromatic H), 6.56 (1H, d,d,d, J=7.1, 5.0, 0.9 Hz, aromatic H), 6.85–7.03 (4H, m, aromatic H), 7.41 (1H, d,d,d, J=8.6, 7.1, 1.9 Hz, aromatic H), 8.09 (1H, d,d,d, J=5.0, 1.9, 0.8 Hz, aromatic H).

Alal. ($C_{18}H_{24}N_4O \cdot \frac{1}{4}H_2O$): Calcd: C, 68.22; H, 7.79; N, 17.68; Found: C, 67.98; H, 7.61; N, 17.07.

The compounds reported in Examples 3–7 were prepared by the acyl chloride method described above in the specification.

EXAMPLE 3

Preparation of 4-(2'-methoxy)phenyl-1-[2'-(N-2''-pyridinyl)-p-iodobenzamido]ethyl piperazine (Compound 1a, Scheme 1)

Amine: 200 mg, 0.64 mmol; $Et_3N$: 160 mg. 2.4 eq; 4-iodobenzoyl chloride: 204 mg, 1.2 eq. yield: 240 mg (69%).

IR (film, $v_{max}$): 2900, 2800, 1650, 1600, 1500, 1250 $cm^{-1}$.

$^1H$ NMR ($CDCl_3$, δ) : 2.63 (4H, br, $NCH_2$), 2.73 (2H, t, J=6.7 Hz, $CONCH_2$—), 2.92 (4H, br, $NCH_2$), 3.84 (3H, s, $CH_3O$—), 4.27 (2H, t, J=6.7 Hz, $CONCH_2CH_2$—), 6.77 (1H, d, J=8.1 Hz, aromatic H), 6.82–7.05 (SH, m, aromatic H), 7.05 (2H, d, J=8.5 Hz, IC=CH), 7.43 (1H, d, d, d, J=8.0, 7.5, 1.9 Hz, aromatic H), 7.54 (2H, d, J=8.6 Hz, COC=CH), 8.43 (1H, d, d, d, J=4.9,2.0,0.8 Hz, aromatic H)

MS: M/Z 543 ($M^+$+1), 527, 417, 351, 311, 218, 205, 162.

Alal. ($C_{25}H_{27}N_4O_2I$): Calcd: C, 55.36; H, 5.02; N, 10.33; Found: C, 55.21; H, 4.99; N, 10.24.

EXAMPLE 4

Preparation of 4-(2'-methoxy)phenyl-1-[2'-(N-2''-pyridinyl)-o-iodobenzamido]ethyl piperazine (Compound 1c, Scheme 1)

Amine: 120mg, 0.38 mmol; $Et_3N$: 85 mg. 2.4 eq; 2-iodobenzoyl chloride: 122 mg, 1.2 eq. yield: 188 mg (90%). JR (film, $v_{max}$): 2900, 2800, 1650, 1600, 1500, 1250 $cm^{-1}$.

$^1H$ NMR ($CDCl_3$, δ): 2.64 (4H, br, $NCH_2$), 2.77 (2H, br, $CONCH_2CH_2$), 2.96 (4H, br, $NCH_2$), 3.83 (3H, s, $CH_3O$—), 4.28 (2H, br, $CONCH_2CH_2$—), 6.85–7.74 (10H, br, aromatic H), 7.76 (1H, d, J=7.7 Hz, aromatic H) 8.40 (1H, br, aromatic H).

MS: M/Z 543 (M++i), 415, 341, 311, 231, 218, 205, 190, 162, 149, 120.

Alal. ($C_{25}H_{27}N_4O_2I$): Calcd: C, 55.36; H, 5.02; N, 10.33; Found: C, 55.43; H, 5.01; N, 10.24.

EXAMPLE 5

Preparation of 4-(2'-methoxy)phenyl-1-[2'-(N-2''-pyridinyl)-p-fluorobenzamido]ethyl piperazine (Compound 1d, Scheme 1)

Amine: 200 mg, 0.64 mmol; $Et_3N$: 160 mg mg. 2.4 eq; 4-fluorobenzoyl chloride: 123 mg, 1.2 eq. yield: 231 mg (83%).

IR (film, $v_{max}$): 3062, 2944, 2813, 1648, 1584, 1498, 1471, 1241 $cm^{-1}$.

$^1H$ NMR ($CDCl_3$, δ): 2.64(4H, br, $NCH_2$), 2.74(2H, t, J=6.7 Hz, $CONCH_2$—), 2.92 (4H, br, $NCH_2$), 3.83 (3H, s, $CH_3O$—), 4.28 (2H, t, J=6.7 Hz, $CONCH_2CH_2$—), 6.74 (1H, d, t, J=8.1, 0.8 Hz, aromatic H), 6.81–7.00 (6H, m, aromatic H), 7.03 (1H, d, d, d, J=7.4, 4.9, 1.0 Hz, aromatic H), 7.33 (2H, d, d, J=8.9, 5.4 Hz, aromatic H), 7.41 (1H, d,d,d, J=8.0, 7.5, 2.0 Hz, aromatic H), 8.42 (1H, d,d,d, J=4.9, 1.9, 0.8 Hz, aromatic H).

Alal. ($C_{25}H_{27}N_4O_2F \cdot \frac{3}{4}H_2O$): Calcd: C,67.02; H,6.41; N,12.51; Found: C,66.80; H,6.11; N,12.37.

EXAMPLE 6

Preparation of 4-(2'-methoxy) phenyl-1-[2'-(N-2''-pyridinyl)-p-nitrobenzamido]ethyl piperazine (Compound 1e, Scheme 1)

Amine: 200 mg, 0.64 mmol; $Et_3N$: 160 mg mg. 2.4 eq; 4-nitrobenzoyl chloride: 143 mg, 1.2 eq. yield: 196 mg (66%). IR (film, $v_{max}$): 3058, 2946, 2815, 1654, 1584, 1521, 1343, 1262 $cm^{-1}$.

$^1H$ NMR ($CDCl_3$, δ): 2.64 (4H, br, $NCH_2$), 2.74 (2H, t, J=6.6 Hz, $CONCH_2$—), 2.93 (4H, br, $NCH_2$), 3.84 (3H, s, $CH_3O$—), 4.27 (2H, t, J=6.6 Hz, $CONCH_2CH_2$—), 6.82–6.92 (4H, m, aromatic H), 6.97 (1H, d,d,d, J=7.9, 6.7, 2.4 Hz, aromatic H), 7.07 (1H, d,d,d, J=7.4, 4.9, 1.0 Hz, aromatic H), 7.46 (1H, m, aromatic H), 7.47 (2H, d,t, J=8.9, 2.2 Hz, aromatic H), 8.04 (2H, d,t, J =8.9, 2.2 Hz, aromatic H), 8.39 (1H, d,d,d, J=4.9, 2.0, 0.8 Hz, aromatic H). Alal. ($C_{25}H_{27}N_5O_4 \cdot \frac{3}{4}H_2O$): Calcd: C, 63.21; H,6.05; N,14.74; Found: C,63.22; H,5.78; N,14.78.

EXAMPLE 7

Preparation of 4-(2'-methoxy)phenyl-1-[2'-(N.2''-pyridinyl)cyclohexylcarbamido]ethyl piperazine (Compound 1f, Scheme 1)

Amine: 100 mg, 0.32 mmol; $Et_3N$: 80 mg. 2.4 eq; cyclohexylcarbonyl chloride: 56 mg, 1.2 eq. yield: 67 mg (50%). IR (film, $v_{max}$): 2900, 2800, 1650, 1600, 1500, 1250 $cm^{-1}$. 1H NMR ($CDCl_3$, δ): 1.01–1.75 (10H, m, cyclohexanyl H), 2.23 (1H, m, $COCH$—), 2.61 (6H, t, j=6.9 Hz, $NCH_2$—), 2.98 (4H, br, $NCH_2$—), 3.83 (3H, s, $CH_3O$—), 3.99

(2H, t, J=6.9 Hz, CONCH$_2$—), 6.84 (1H, d, J=7.7 Hz, aromatic H), 6.90 (2H, d,d, J=5.0, 0.8 Hz, aromatic H), 6.98 (1H, m, aromatic H), 7.23 (1H, d,d,d, J=7.4, 5.0, 0.9 Hz, aromatic H), 7.29 (1H, d, J=7.9 Hz, aromatic H), 7.75 (1H, t, d, J=7.7, 2.0 Hz, aromatic H), 8.52 (1H, d,d,d, J=4.8, 1.8, 0.6 Hz, aromatic H).

MS: M/Z 423 (M$^+$+1), 407,311,274,218,205, 162.

Alal. (C25H34N4O2): Calcd: C, 71.06; H, 8.11; N, 13.26; Found: C, 70.95; H, 8.17; N, 13.16.

EXAMPLE 8

Preparation of 4-(2'-methoxy)phenyl-1-[2'-(N-2"-pyridinyl)-m-iodobenzamido]ethyl piperazine (Compound 1b, Scheme 1)

This compound was prepared by the acid method described above in the specification. Amine: 120 mg, 0.38 mmol; Et$_3$N: 0.3 mL, 3 eq; 3-iodobenzoic acid: 114 mg, 1.2 eq. yield: 180 mg (87%).

IR (film, v$_{max}$): 3062, 2938, 2811, 1652, 1582, 1465 cm$^{-1}$.
$^1$H NMR (CDCl$_3$, δ): 2.63 (4H, br, NCH$_2$), 2.71 (2H, t, J=6.7 Hz, CONCH$_2$—), 2.93 (4H, br, NCH$_2$), 3.84 (3H, s, CH$_3$O—), 4.27 (2H, t, J=6.7 Hz, CONCH$_2$CH$_2$—), 6.79–6.99 (6H, m, aromatic H), 7.06 (1H, d,d,d, J=7.4, 4.9, 1.0 Hz, aromatic H), 7.21 (1H, d,t, J=7.8, 1.1 Hz, aromatic H), 7.45 (1H, d,d,d, J=8.0, 7.6, 2.0 Hz, aromatic H), 7.61 (1H, d,d,d, J=7.8, 1.7, 1.1 Hz, aromatic H). 7.73 (1H, t, J=0.7-Hz, aromatic H), 8.43 (1H, d,d,d, J=4.9, 1.9, 0.8 Hz, aromatic H).

MS: M/Z 543 (M++I), 415, 272, 231, 205, 162, 149, 119, 105.

Alal. (C$_{25}$H$_{27}$N$_4$O$_2$I): Calcd: C, 55.36; H, 5.02; N, 10.33; Found: C, 55.45; H, 5.06; N, 10.27.

The aromatic tin compounds reported in Examples 9 and 10 were prepared as follows:

To a mixture of aromatic iodo compound and (Ph$_3$P)$_4$Pd in Et$_3$N was added Bis(tributyltin) in neat. The mixture was stirred at 90° C. for 16 hours. Et$_3$N was removed on vacuum and the residue was purified by PTLC (EtOAc as developing solvent) to give pure product.

EXAMPLE 9

Preparation of 4-(2'-methoxy)phenyl-1-[2'-(N-2"-pyridinyl)-p-tributylstannylbenzamido]ethyl piperazine (Compound 1g, Scheme 1)

1a:30 mg, 0.06 mmol; (Ph$_3$P)$_4$Pd: 4 mg; (SnBu$_3$)$_2$:0.4 mL; Et$_3$N: 0.4 mL. Yield: 12 mg (31%) IR (film, v$_{max}$): cm$^{-1}$.

$^1$H NMR (CDCl$_3$, δ): 0.85 (9H, t, J=7.3 Hz, CHCH$_2$—), 1.00 (6H, m, SnCH$_2$—), 1.27 (6H, hex, J=7.1 Hz, CH$_3$CH$_2$—), 1.46 (6H, m, SnCH$_2$CH$_2$—), 2.65 (4H, br, —NCH$_2$CH$_2$N—), 2.75 (2H, t, J=6.8 Hz, —CONCH$_2$CH$_2$—), 2.93 (4H, br, —NCH$_2$CH$_2$N—), 3.84 (3H, s, CH$_3$O—), 4.30 (2H, t, J=6.7 Hz, CONCH$_2$CH$_2$—), 6.76 (1H, d, J=8.1 Hz, aromatic H), 6.82–7.02 (5H, m, aromatic H), 7.24 (2H, d, J=8.1 Hz, SnC=CH), 7.29 (2H, d, J=8.1 Hz, SnC=CHCH=), 7.36 (1H, m, aromatic H, 8.42 (1H, d,d,d, J=4.9, 2.0, 0.8 Hz, aromatic H).

EXAMPLE 10

Preparation of 4-(2'-methoxy)phenyl-1-[2'-(N-2"-pyridinyl)-m-tributylstannylbenzamido]ethyl piperazine (Compound 1b, Scheme 1)

1b:30 mg, 0.06 mmol; (Ph$_3$P)4Pd: 4 mg; (SnBu$_3$)$_2$:0.4 mL; Et$_3$N: 0.4 mL. Yield:22 mg (57%) IR (film, v$_{max}$): 2952, 2929, 1648, 1584, 1465, 1237 cm$^{-1}$.

$^1$H NMR (CDCl$_3$, δ): 0.86 (9H, t, J=7.1 Hz, CH$_3$CH$_2$—), 0.92 (6H, m, SnCH—), 1.27 (6H, hex, J=7.1 Hz, CH$_3$CH$_2$—), 1.43 (6H, m, SnCH$_2$CH$_2$—), 2.65 (4H, br, —NCH$_2$CH$_2$N—), 2.76 (2H, t, J=6.6 Hz, —CONCH$_2$CH$_2$—), 2.93 (4H, br, —NCH$_2$CH$_2$N—), 3.83 (3H, s, CH$_3$O—), 4.31 (2H, t, J=6.6 Hz, CONCH$_2$CH$_2$—), 6.72 (1H, d, J=8.1 Hz, aromatic H), 6.85–7.00 (5H, m, aromatic H), 7.26–7.43 (5H, m, aromatic H), 8.42 (1H, d,d,d, J=4.8, 1.9, 0.8 Hz, aromatic H).

EXAMPLE 11

Preparation of [$^{123}$I]1a (MPPI) and 1b

No-carrier-added [$^{123}$I]1a (MPPI) and 1b were prepared by an iododestannylation reaction similar to the procedure reported previously (Chumpradit et al., "Iodinated Tomoxetine Derivatives as Selective Ligands for Serotonin and Norepinephrine Uptake Sites", *J. Med. Chem.* 35: 4492–4497 (1992)). Hydrogen peroxide (50 µl, 3% w/v) was added to a mixture of 50 µl of tributyltin precursor (5–10 mg/mi EtOH), 50 µl of 1N HCl and $^{123}$I sodium iodide (2–20 mCi) in a sealed vial. The reaction was allowed to proceed for 20 minutes at room temperature, and was then terminated by addition of 0.1 ml of saturated sodium bisulfite. The reaction mixture was extracted with ethyl acetate (3×1 ml) after neutralization with saturated NaHCO$_3$ solution. The extracted ethyl acetate layers were evaporated to dryness, and the remaining residue was dissolved in EtOH and purified by HPLC using a reverse phase column (PRP-1 column, Hamilton Co., Reno, Nev.) eluted with an isocratic solvent of 80% acetonitrile-20% pH 7.0 buffer (5 mM 3,3,-dimethylglutaric acid); the retention time was 9 minutes (1 ml/min). The fractions containing the desired product were collected, condensed and re-extracted with ethyl acetate (3×1 ml). The final product of no-carrier-added (yield 70–80%; purity >98%) was evaporated to dryness and redissolved in 100 µl of 50% EtOH with 100 µg of ascorbic acid added as an anti-oxidant.

The final product [$^{123}$I]1a and 1b, was stored at −20° C. The stability of the product was evaluated from three preparations and was found to be stable for at least four weeks (>95% pure, analyzed by HPLC).

EXAMPLE 12

Determination of Binding Affinities

The 5-HT$_{1A}$ binding affinity of p-, m-, o- MPPI, p-fluoro- and p-nitro-MPP derivatives (1a–f) in rat hippocampal membrane preparations with [$^{125}$I](R,S)trans-8-OH-PIPAT as the ligand were observed and are reported in Table I. All of the five benzamide derivatives displayed similar potency (Ki=1–3.3 nM) as that for compound WAY 100635 (Ki=0.8 nM), except o-MPPI, 1c, which exhibited lower affinity (Ki=10 nM).

TABLE I

Inhibition constants of compounds on the binding of [$^{125}$I]-8-OH-PIPAT to rat hippocampal homogenates[8]

| Compounds | | Ki (nM) |
|---|---|---|
| 1a | (p-MPPI)* | 2.6 ± 0.7 |
| 1b | (m-MPPI) | 1.7 ± 0.1 |
| 1c | (o-MPPI) | 10.4 ± 0.8 |
| 1d | (p-MPPF) | 3.3 ± 0.8 |
| 1e | (p-MPPN) | 1.6 ± 0.6 |
| 1f | (WAY 100635) | 0.84 ± 0.1 |
| 1g** | | 6.08 ± 0.8 |

*Kd = 0.3 nM for [$^{125}$I]-MPPI, 1a, to rat hippocampal homogenates (Kung, Unpublished data)
**1g = 4-(2'-methoxy)phenyl-1-[2'-(N-2"-pyrimidinyl)-p-iodobenzamido] ethyl piperazine Similarly, the 5-HT$_{1A}$ binding affinity of p-; m- and O-MPPI in rat hippocampal membrane preparations with [$^{125}$I]p-MPP as the ligand were observed and are reported in Table II.

TABLE II

Inhibition Constants of Compounds on the Binding of [$^{125}$I]-p-MPP Binding to the Rat Hippocampal Homogenates

| Compound | Ki (nM) |
|---|---|
| (±8-OH-DPAT) | 2.3 ± 0.2 |
| WB 4101 | 5.0 ± 0.5 |
| 5-HT | 2.6 ± 0.7 |
| WAY-100635 | 0.38 ± 0.05 |
| p-MPPI | 0.96 ± 0.10 |
| m-MPPI | 2.46 ± 0.14 |
| o-MPPI | 8.18 ± 2.2 |
| spiperone | 12.2 ± 2.2 |
| hetanserin | 1970 ± 98 |

EXAMPLE 13

Evaluation of Biodistribution in Rats

Male Spmgue-Dawley rats (225–300 g), allowed free access to food and water, were used for an in vivo biodistribution study. While the rats were under ether anesthesia, 0.2 mL of a saline solution containing [$^{123}$I]1a and 1b (8–10 μCi) was injected directly into the femoral vein, and rats were sacrificed at various time points postinjection by cardiac excision under ether anesthesia. The organs of interest were removed and weighed and the radioactivity was counted with a Packard gamma automatic counter (Model 5000). The percentage dose per organ was calculated by a comparison of the tissue counts to suitably diluted aliquots of the injected material. Total activities of blood and muscle were calculated under the assumption that they were 7% and 40% of the total body weight, respectively.

Regional brain distribution in rats was obtained after an iv injection of [$^{123}$I]1a and 1b. By dissecting, weighing and counting samples from different brain regions (cortex, striatum, hippocampus, hypothalamus and cerebellum), the percentage dose/gram of the sample was calculated by comparing the sample counts with the count of the diluted initial dose. Results are presented in Tables III and IV and in FIGS. 2a, 2b, and 2c and FIGS. 3A, 3B, and 3C.

TABLE III

Biodistribution in rats after an iv injection of [$^{123}$I] 1a, (% dose/organ, average of 3 rats ± SD)

| Organ | 2 min | 30 min | 60 min | 120 min |
|---|---|---|---|---|
| Blood | 4.49 ± 0.55 | 4.04 ± 1.24 | 2.73 ± 0.09 | 2.05 ± 0.30 |
| Heart | 0.91 ± 0.09 | 0.18 ± 0.04 | 0.13 ± 0.02 | 0.07 ± 0.003 |
| Muscle | 11.29 ± 4.15 | 7.58 ± 2.48 | 4.34 ± 0.91 | 2.14 ± 0.15 |
| Lung | 2.39 ± 0.10 | 0.48 ± 0.05 | 0.31 ± 0.04 | 0.18 ± 0.002 |
| Kidney | 5.20 ± 0.44 | 1.74 ± 0.49 | 1.06 ± 0.23 | 0.62 ± 0.11 |
| Spleen | 0.37 ± 0.13 | 0.14 ± 0.02 | 0.11 ± 0.04 | 0.07 ± 0.009 |
| Liver | 14.2 ± 3.1 | 8.71 ± 0.20 | 7.53 ± 0.99 | 5.16 ± 1.01 |
| Skin | 8.34 ± 1.22 | 8.24 ± 1.60 | 4.51 ± 1.00 | 5.82 ± 4.37 |
| Thyroid | 0.09 ± 0.02 | 0.03 ± 0.02 | 0.02 ± 0.007 | 0.02 ± 0.01 |
| Brain | 1.22 ± 0.22 | 0.22 ± 0.01 | 0.12 ± 0.005 | 0.05 ± 0.002 |
| Regional distribution (% dose/gm) | | | | |
| Region | | | | |
| cerebellum | 0.64 ± 0.08 | 0.07 ± 0.006 | 0.04 ± 0.001 | 0.024 ± 0.0002 |
| hypothalamus | 0.67 ± 0.10 | 0.14 ± 0.04 | 0.051 ± 0.004 | 0.030 ± 0.0002 |
| striatum | 0.76 ± 0.12 | 0.09 ± 0.0001 | 0.046 ± 0.004 | 0.021 ± 0.0007 |
| hippocampus | 0.87 ± 0.18 | 0.23 ± 0.007 | 0.127 ± 0.009 | 0.040 ± 0.003 |
| cortex | 0.91 ± 0.06 | 0.11 ± 0.01 | 0.061 ± 0.002 | 0.026 ± 0.002 |

P.C = 1800(octanol/0.1M phosphate, pH 7.0)

TABLE IV

Biodistribution in rats after an iv injection of [$^{123}$I] 1b (% dose/organ, average of 3 rats ± SD)

| | 2 min | 30 min | 60 min | 120 min |
|---|---|---|---|---|
| Organ | | | | |
| Blood | 5.06 ± 0.32 | 2.27 ± 0.24 | 1.21 ± 0.08 | 1.08 ± 0.13 |
| Heart | 0.77 ± 0.08 | 0.11 ± 0.008 | 0.05 ± 0.005 | 0.03 ± 0.003 |
| Muscle | 14.98 ± 1.16 | 10.13 ± 4.90 | 4.75 ± 1.76 | 5.56 ± 3.54 |
| Lung | 1.87 ± 0.08 | 0.31 ± 0.004 | 0.13 ± 0.02 | 0.10 ± 0.004 |
| Kidney | 3.67 ± 0.22 | 1.18 ± 0.11 | 0.54 ± 0.007 | 0.36 ± 0.008 |
| Spleen | 0.68 ± 0.12 | 0.09 ± 0.01 | 0.04. ± 0.006 | 0.029 ± 0.002 |
| Liver | 25.72 ± 3.29 | 8.04 ± 0.63 | 4.58 ± 0.30 | 4.13 ± 0.44 |
| Skin | 10.16 ± 3.32 | 13.71 ± 0.52 | 5.85 ± 1.99 | 3.66 ± 0.68 |
| Thyroid | 0.07 ± 0.02 | 0.06 ± 0.02 | 0.05 ± 0.02 | 0.11 ± 0.07 |
| Brain | 0.76 ± 0.05 | 0.07 ± 0.004 | 0.02 ± 0.006 | 0.016 ± 0.0005 |
| Regional distribution (% dose/gm) | | | | |
| Region | | | | |
| cerebellum | 0.47 ± 0.01 | 0.039 ± 0.003 | 0.014 ± 0.004 | 0.008 ± 0.0004 |
| hypothalamus | 0.50 ± 0.04 | 0.042 ± 0.003 | 0.015 ± 0.005 | 0.010 ± 0.002 |
| striatum | 0.51 ± 0.003 | 0.042 ± 0.004 | 0.012 ± 0.003 | 0.006 ± 0.0008 |
| hippocampus | 0.54 ± 0.03 | 0.051 ± 0.005 | 0.013 ± 0.004 | 0.006 ± 0.001 |
| cortex | 0.50 ± 0.03 | 0.043 ± 0.002 | 0.015 ± 0.005 | 0.008 ± 0.0008 |

Biodistribution of the $^{123}$I labeled agents in rats displayed good initial brain uptake (total brain uptake was 1.22 and 0.76% dose/organ for 1a and 1b, respectively, at 2 min after iv injection). Surprisingly, the regional distribution pattern in rat brain showed that only the para derivative, 1a, displayed the 5-HT$_{1A}$ related specific uptake. Uptake in hippocampal tissue, where the 5-HT$_{1A}$ receptor density is high, was 0.13 and 0.013% dose/g for 1a and 1b, respectively, at 60 minutes after the iv injection. In view of the relatively similar binding affinity and structure of the para- and meta-derivatives, 1a and 1b, the apparent disparity in the in vivo biodistribution in rat brain is unexpected. Different bioavailability for these two close analogs may have significant implication in the future in using this series of agents as in vivo imaging ligands as well as therapeutic agents.

These tests suggest that [$^{125}$I]-MPPI, and the other compounds of this invention, may provide excellent probes for the investigation and characterization of 5-HT$_{1A}$ receptors. The corresponding [$^{123}$I] and [$^{18}$F] (T$_{1/2}$=110 min, γ energy 511 kev after positron annihilation) labeled 1a and 1d, respectively, may provide potentially useful ligands for in vivo imaging of the 5-HT$_{1A}$ receptor density in brain with single photon emission computed tomography and positron emission tomography.

EXAMPLE 14

Blocking Studies

Figure 4A:
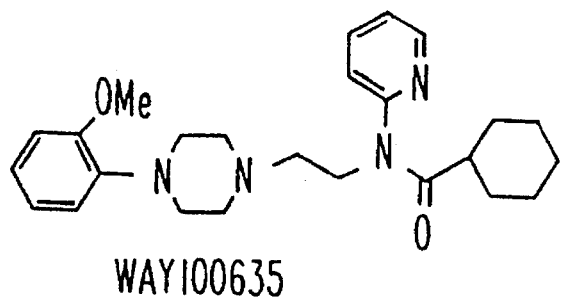
FIGS. 4A, 4B, and 4C illustrate changes of ratios of regional brain uptake of [$^{123}$I]p-MPPI in rats, with no pre-treatment (control) or after pre-treatment with WAY100635 or 8-OH DPAt.
Figure 4B:
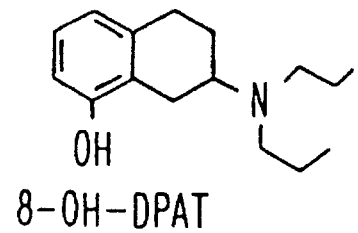
Figure 4C:
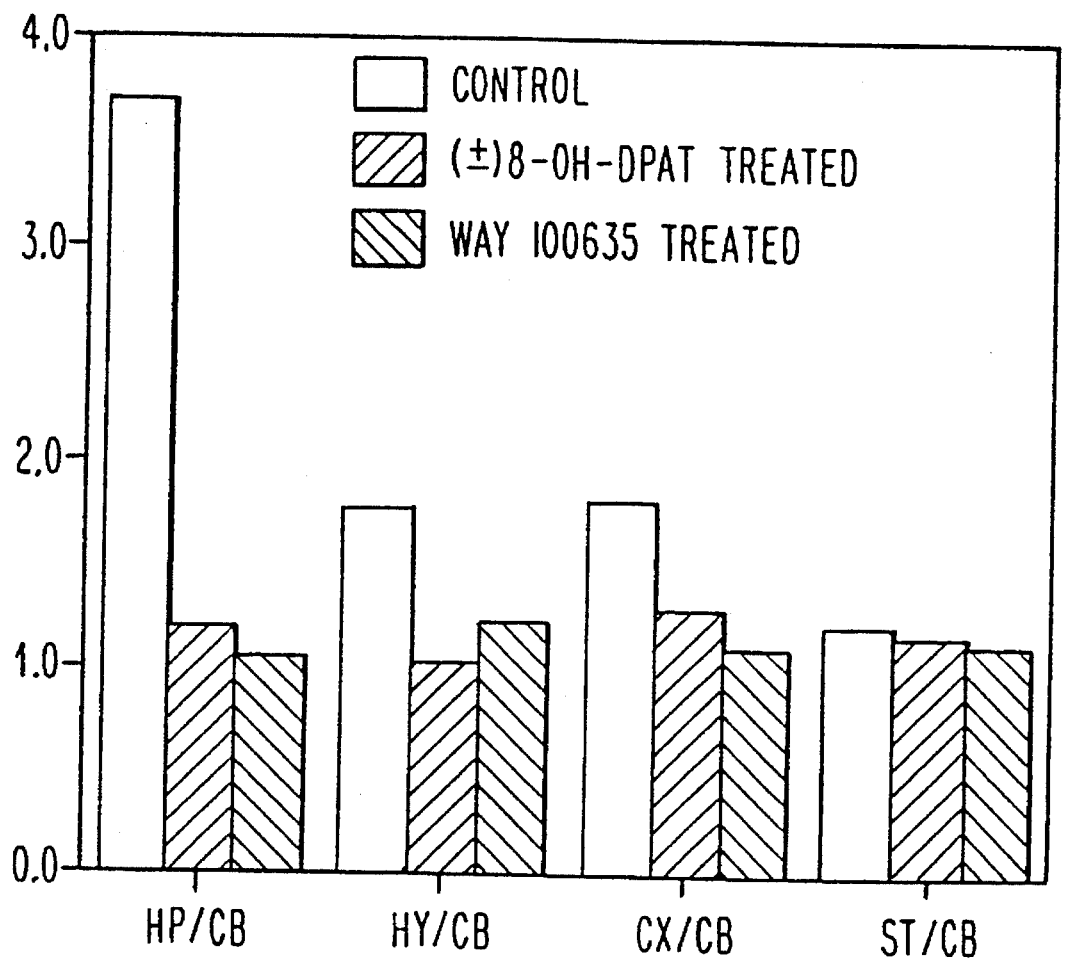

In order to further characterize the in vivo brain uptake of 1a in rats, blocking studies were carried out to determine changes of the ratios of regional brain uptake. A tracer dose of [$^{123}$I] or [$^{125}$I]1a was injected in rats and, at 30 minutes post iv injection, they were sacrificed and regional brain uptake (% injected dose/gram of brain tissue, n=3–4) was determined. Ratios for each region were calculated based on the % dose/gram of each region divided by the same in CB. Blocking studies were performed in rats pretreated with (±)8-OH-DPAT (2mg/kg, iv) or WAY 100635 (1 mg/kg, iv) at 5 and 20 minutes prior to the injection of the tracer, respectively. minutes prior to the injection of the tracer, respectively. With pretreatment of either an agonist, (±)8-OH-DPAT, or an antagonist, WAY 100635, the specific uptake in the hippocampus region of the brain displayed a mark decrease; the HP/CB ratio changed from 3.69 (control) to 1.21 ((±)8-OH-DPAT treated) and 1.07 (WAY 100635 treated). The dramatic decrease is most likely due to the competition of (±)8-OH-DPAT or WAY 100635 binding to the same 5-HT$_{1A}$ receptor in the brain. Results of these studies are presented in FIGS. 4a, 4b, and 4c. (HP: hippocampus; CB: cerebellum; HY: hypothalamus; CX: cortex; ST: striatum).

What is claimed is:

1. Compounds of the formula

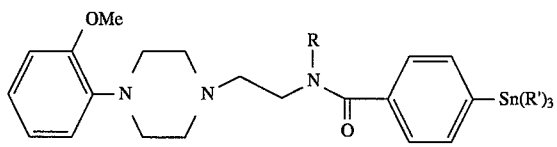

where

R' is a C$_1$–C$_5$ alkyl group;

R is selected from the group consisting of

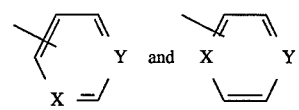

X and Y are independently selected from the group consisting of N and CH, provided that at least one of X or Y is N.

2. A compound of claim 1 where R is 2-pyridyl.

3. A kit for preparing an imaging agent comprising a vial containing a physiologically suitable solution of a compound of claim 1 and a vial containing a radioisotope selected from the group consisting of $^{125}$I, $^{123}$I, $^{123}$I, $^{18}$F, $^{77}$Br, and $^{76}$Br, and an oxidant.

4. A method of imaging serotonin 5-HT$_{1A}$ receptors in a patient comprising administering to said patient an imaging effective quantity of an imaging agent of the formula

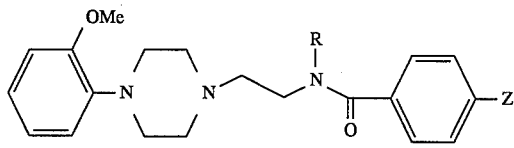   I where
Z is selected from the group consisting of a radioactive iodine, bromine and fluorine isotope;
R is selected from the group consisting of

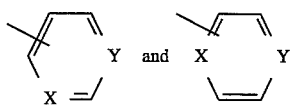

X and Y are independently selected from the group consisting of N and CH, provided that at least one of X and Y is N;
and pharmaceutically acceptable salts thereof; and measuring the gamma ray or photo emissions therefrom.

5. A method of imaging serotonin 5-HT$_{1A}$ receptors in a patient comprising administering to said patient an imaging effective quantity of an imaging agent of the formula

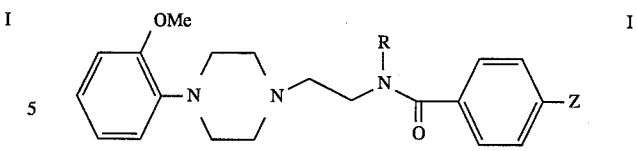   I where
Z is selected from the group consisting of radioactive iodine, bromine and fluorine isotope;
R is pyridyl;
X and Y are independently selected from the group consisting of N and CH, provided that at least one of X and Y is N;
and pharmaceutically acceptable salts thereof;
and measuring the gamma ray or photo emissions therefrom.

6. A method of imaging serotonin 5-HT$_{1A}$ receptors in a patient comprising administering to said patient an imaging effective quantity of the imaging agent [$^{123}$I]-4-(2'-methoxy)phenyl-[2'-(N-2"-pyridinyl)-p-iodobenzamido]ethyl-piperazine and measuring the gamma ray or photo emissions therefrom.

* * * * *